United States Patent
Karas et al.

(10) Patent No.: US 10,548,912 B2
(45) Date of Patent: Feb. 4, 2020

(54) DOSAGE REGIMEN FOR A TIACUMICIN COMPOUND

(71) Applicant: Astellas Pharma Europe Ltd., Chertsey, Surrey (GB)

(72) Inventors: Andreas Johannis Karas, Surrey (GB); Christopher Mark Longshaw, Surrey (GB); Leticia Delgado-Herrera, Surrey (GB); Bernhardt George Zeiher, Surrey (GB)

(73) Assignee: Astellas Pharma Europe Ltd., Chertsey, Surrey (GB)

( * ) Notice: Subject to any disclaimer, the term of this patent is extended or adjusted under 35 U.S.C. 154(b) by 0 days.

(21) Appl. No.: 15/741,656

(22) PCT Filed: Jul. 4, 2016

(86) PCT No.: PCT/EP2016/001140
§ 371 (c)(1),
(2) Date: Jan. 3, 2018

(87) PCT Pub. No.: WO2017/005358
PCT Pub. Date: Jan. 12, 2017

(65) Prior Publication Data
US 2018/0193370 A1    Jul. 12, 2018

(30) Foreign Application Priority Data
Jul. 3, 2015 (EP) .................... 15075021

(51) Int. Cl.
*A61K 31/7048* (2006.01)
*A61K 9/00* (2006.01)
*A61P 31/04* (2006.01)
*G01N 33/569* (2006.01)

(52) U.S. Cl.
CPC ........ *A61K 31/7048* (2013.01); *A61K 9/0053* (2013.01); *A61P 31/04* (2018.01); *G01N 33/56916* (2013.01)

(58) Field of Classification Search
CPC ............. A61K 31/7048; A61K 9/0053; G01N 33/56916; A61P 31/04
USPC ......................................... 514/28; 424/164.1
See application file for complete search history.

(56) References Cited

U.S. PATENT DOCUMENTS

2007/0105791 A1* 5/2007 Sears ............... A61K 31/70
514/35
2012/0276059 A1* 11/2012 Boone ............. G01N 33/56911
424/93.4

OTHER PUBLICATIONS

McFarland et al. Breaking the Cycle: Treatment Strategies for 163 Cases of Recurrent Clostridium difficile Disease. American Journal of Gastroenterology vol. 97, No. 7, p. 1769-1775, 2002. (Year: 2002).*
Chilton et al., "Efficacy of alternative fidaxomicin dosing regimens for treatment of simulated Clostridium difficile infection in an in vitro human gut model", J. Antimicrob Chemother, 70: 2598-2607 (2015).
Chilton et al. "Efficacy of tapered fidaxomicin dosing regimens to treat simulated Clostridium difficile infection (CDI) in an in vitro gut model", Poster (2014).
Soriano et al., "Novel fidaxomicin treatment regimens for patients with multiple Clostridium difficile infection recurrences that are refractory to standard therapies", Open Forum Infectious Diseases, 1: 1-21 (2014).
Chilton et al., "Comparison of Extended Duration fidaxomicin dosing regimens for treatment of Clostridium difficile infection (CDI) in an in vitro gut model", 2013:K-336.
Golan et al., "Safety and efficacy of fidaxomicin in the treatment of Clostridium difficile-associated diarrhea", Therapeutic Advances in Gastroenterology, 5: 395-402 (2012).
McFarland et al., "Breaking the cycle: Treatment strategies for 163 cases of recurrent Clostridium difficile disease", American Journal of Gastroenterology, 97: 1769-1775 (2002).

* cited by examiner

Primary Examiner — Yih-Horng Shiao
(74) Attorney, Agent, or Firm — Morgan, Lewis & Bockius LLP

(57) ABSTRACT

The present inventors provides one or more of a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed. Further the invention provides the use of the tiacumicin compound to reduce recurrence in a patient suffering from CDI or CDAD.

21 Claims, No Drawings

DOSAGE REGIMEN FOR A TIACUMICIN COMPOUND

TECHNICAL FIELD

The present invention relates to a novel dosage regimen of a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient, the use of the novel dosage regimen for the oral treatment of CDI or CDAD and the reduction of recurrence of CDI or CDAD in a patient after the end of the treatment.

BACKGROUND ART

Tiacumicin compounds, especially Fidaxomicin, are indicated for the treatment of *Clostridium difficile* infections (CDI) also known as *Clostridium difficile*-associated disease (CDAD) and prevention of recurrences. CDI is a major burden on healthcare facilities worldwide (Wiegand P. N., Nathwani D., Wilcox M. H. et al. in J. Hosp Infect of 10 Apr. 2012; Ghantoji S. S., Sail, K. Lairson D. R. (2010) in J. Hosp. Infect. 74: 309-318).

These infections are normally caused by changes in the composition and function of the intestinal flora following the use of antimicrobials and are called antibiotic-associated diarrhea (AAD). *Clostridium difficile* infections (CDI) also known as *C. difficile*-associated disease (CDAD) refer to a wide spectrum of diarrheal illnesses caused by the toxins produced by this organism, including cases of severe colitis with or without the presence of pseudomembranes.

The occurrence of AAD varies greatly and is influenced by a number of factors, including nosocomial outbreaks, patterns of antimicrobial prescription, and individual susceptibility. It is estimated that 10% to 15% of all hospitalized patients treated with antibiotics will develop AAD. Most important, twice as many will become asymptomatic carriers. Risk factors include compromised immune status, advanced age, abdominal surgery, co morbidity, types and prolonged use of antibiotics, reduced gastric acid, and the length of hospitalization. For example, infection rates for *Clostridium difficile* are reported to be around 10% after 2 weeks of hospitalization but may reach 50% after 4 or more weeks (McFarland L V. Epidemiology, risk factors and treatments for antibiotic-associated diarrhea. Dig Dis 1998; 16:292-307)

All groups of antibiotics may cause AAD, but those with broad-spectrum coverage—in particular cephalosporins, fluoroquinolones, extended-coverage penicillins, and clindamycin—are the most common culprits (Wistrom J, Norrby S R, Myhre E, et al. Frequency of antibiotic-associated diarrhoea in 2462 antibiotic-treated hospitalized patients: a prospective study. J Antimicrob Chemother 2001; 47:43-50).

Treatment options are limited and are associated with high rates of recurrence.

Tiacumicin compounds are naturally occurring compounds with an antibiotic activity that can be obtained by cultivating various microorganisms belonging to the Actinoplanes family (especially the genus *Dactylosporangium aurantiacum*, subspecies *hamdenensis*) in a suitable nutrient medium at a suitable temperature and isolating the compounds having antibiotic activity against a variety of microorganisms (tiacumicins A-F; U.S. Pat. No. 4,918,174).

Especially tiacumicins B and C turned out to possess antibiotic activity against a number of Gram-positive bacteria in vitro including strains resistant to therapeutic antibiotics, used at the time.

U.S. Pat. No. 5,583,115 discloses dialkyltiacumicin compounds, which are derivatives of the above-mentioned tiacumicin compounds A-F, were found to have in vitro activity against a variety of bacterial pathogens and in particular against *Clostridium* species.

U.S. Pat. No. 5,767,096 discloses bromotiacumicin compounds, which are also derivatives of tiacumicin compounds A-F, which were found to have in vitro activity against some bacterial pathogens and in particular against *Clostridium* species.

From a chemical point of view the tiacumicins share an 18-membered macrocyclic ring, which is glycosidically attached to one or two optionally substituted sugar molecules (U.S. Pat. No. 4,918,174 and WO 2004/014295) as follows (formula I):

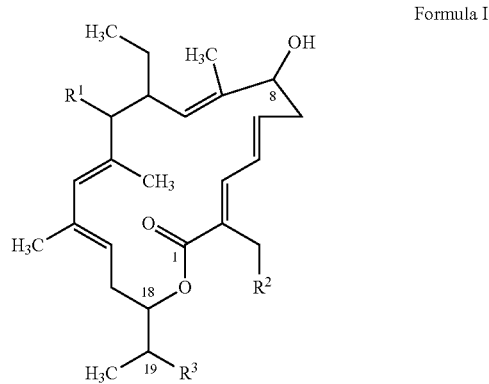

Formula I

WO 2004/014295 describes substantially pure R-tiacumicins, obtained by submerged aerobic fermentation of *Dactylosporangium aurantiacum hamdenensis*.

WO 2006/085838 discloses pharmaceutical compositions containing R-tiacumicins and especially R-tiacumicin B (also known under the name Fidaxomicin), which contains an R-hydroxy-group at C19, which shows surprisingly lower MIC (MIC stand for minimal inhibitory concentration) values when tested in vitro against *Clostridium* species than the optically pure S-isomer of tiacumicin B and other tiacumicin related compounds.

According to an in vitro BCS (Biopharmaceutics Classification System) study, fidaxomicin is a BCS Class IV compound (low solubility, low permeability). Upon oral administration fidaxomicin is poorly absorbed from the intestinal tract and is therefore associated with a low incidence of systemic side effects.

Tablets containing 200 mg fidaxomicin are commercially available in Europe (under the trademark Dificlir) and in the USA (under the trademark Dificin).

Fidaxomicin is indicated for the treatment of *Clostridium difficile* infections (CDI) also known as *C. difficile*-associated disease (CDAD) and prevention of recurrences.

In two Phase III randomised, double-blind, clinical trials, fidaxomicin demonstrated non-inferiority to vancomycin for initial clinical cure of CDI, but superiority in reduction of recurrence and sustained clinical response (Crook et al. (2012) in Clin. Infect. Dis. 55(Suppl 2): S93-103).

In phase III clinical trials the risk of fidaxomicin or vancomycin treatment failure doubled for each treatment day less than 10 days (T. Louie et al. Poster presented at 22$^{nd}$ European Congress of Clinical Microbiology & Infectious Diseases, March 31-Apr. 3, 2012, London). The relatively low impact of fidaxomicin on gut microflora may allow better recovery of bacteria during prolonged treatment periods, so reducing risk of CDI recurrence (T. J. Louie et al. (2012) in Clin. Infect. Dis. 55(S2) S132-142; Tannock in Microbiology (2010), 156, 3354-3359 (Phase II trials)).

The management of *Clostridium difficile* infections (CDI), thus, is complicated by high recurrence rates with over 50% of second episodes experiencing a recurrence (RCDI=recurrence of *Clostridium difficile* infections). Guidelines recommend managing multiple recurrences with a vancomycin taper. No clear recommendation is available for patients failing this approach. In a recent case series report (Soriano et al in Exp Rev Antiinf Ther 2013; 11:767-776), patients with multiple RCDI that were refractory to vancomycin taper therapy were given either fidaxomicin 200 mg BID for 10 days (FID-TX), or a repeat of CDI treatment followed by either a 10-day fidaxomicin regimen as a chaser (FID-CH), or a taper as 200 mg daily for 7 days, followed by 200 mg QOD for 7-26 days (FID-TP). Demographic information, CDI history, treatment outcomes, and symptom-free interval (SFI) were collected from patient records. Treatment success was considered if symptoms resolved by the end of therapy and no additional antibiotic was needed. RCDI (stand for recurrence of CDI) was defined by the onset of CDI symptoms following successful treatment for a previous episode. 14 patients received 18 courses of fidaxomicin for RCDI (mean age of 60, mean of 4.6 previous CDI episodes, mean of 2.3 previous vancomycin taper courses). All 18 courses resulted in treatment success (3 courses as FID-TX, 8 as FID-CH, and 7 as FID-TP). Of 3 FID-TX courses, there were 2 RCDI episodes (66%). When excluding RCDI due to antimicrobial exposure, there were 2 RCDI (25%) observed after the 8 FID-CH courses and no RCDI following the 7 FID-TP courses. The average SFI following a vancomycin taper was 37 days. The average SFI following FID-TX, FID-CH, and FID-TP was 73, 240, and 150 days, respectively. Patients with RCDI that failed multiple vancomycin tapers had symptom resolution following fidaxomicin therapy. All 3 regimens provided a greater SFI compared to a vancomycin taper. No patient experienced RCDI following FID-TP. FID-CH had the longest SFI, yet follow-up time with FID-TP was shorter given more recent adoption of this regimen. These results suggest the utility of using fidaxomicin to treat RCDI. (M. M. Soriano et al. Abstract 42591; presentation No. 1410; IDWeek, 5 Oct. 2013).

The currently recommended treatment regimen for adults and elderly people (65 years and older) is 200 mg administered twice daily (q12h) for 10 days.

A couple of dosage regimens were already tested for their activity in an in-vitro gut model such as the effectiveness of long (Model A: 200 mg BID during 20 days) versus short pulsed (Model B: 200 mg BID during 5 days, rest during 5 days and 5 days 200 mg BID) course fidaxomicin using a validated CDI model was investigated. Results are available for this model (C. H. Chilton et al. (2013) in J. Antimicrobial Chemotherapy Advance Access September 2013 and C. H. Chilton et al., abstract 23$^{rd}$ European Congress of Clinical microbiology & Infectious Disease, Apr. 27-30, 2013, Berlin).

Various Fidaxomicin dosing regimens were tested in an in vitro human gut model simulating CDI or CDAD. However it is unknown whether or not these dosing regimens will be effective if administered to patients as required by the present invention (C. H. Chilton et al (2014) in J. Antimicrobial Chemotherapy, 70:2598-2607 and C. H. Chilton (14 May 2014), poster presentation P0797)

In addition a comparison between two other models being model A: 200 mg Fidaxomicin BID for 5 days, followed by five days rest then again 200 mg Fidaxomicin once daily for further 10 days was compared with a model B providing 200 mg Fidaxomicin BID for 5 days followed by a single 200 mg Fidaxomicin dose every other day (Poster P0797 presented during poster session on 11 May 2014 during ECCMID congress in Barcelona).

None of the above cited dosage regimens have solved the issue of the high recurrence of CDI or CDAD. In the present invention recurrence is defined as a reappearance of >3 diarrheal stools per 24-hour period within 30 days of end of treatment (EOT), the presence of *Clostridium difficile* toxins A or B, or both, in stool and the need for re-treatment for CDI.

There are various indicators of CDI or CDAD available if tested positive alone or in combination to diagnose *Clostridium difficile* infections. Suitable indicators are for example the consistency of stools, the frequency of diarrhea, the presence of *Clostridium difficile* toxin A (TcdA) or toxin B (TcdB toxin), the presence of the *Clostridium difficile* toxin A gene (tcdA) or B gene (tcdB) and the presence of the *Clostridium difficile* surface antigen (GDH=glutamate dehydrogenase).

An accepted model to those skilled in the art is the Bristol Stool form scale as published by S. J. Lewis et al. In *Scandinavian Journal of Gastroenterology*, 1997, Vol. 32, No. 9, pages 920-924. In table 1 of this publication the seven types of the Bristol stool form scale are defined wherein type 7 is a watery stool and type 1 are separate hard lumps.

| Bristol Stool Form Scale | |
| --- | --- |
| Type 1 | Separate hard lumps, like nuts. |
| Type 2 | Sausage-shaped but lumpy |
| Type 3 | Like a sausage or snake but with cracks on its surface |
| Type 4 | Like a sausage or snake, smooth and soft |
| Type 5 | Soft blobs with clear-cut edges. |
| Type 6 | Fluffy pieces with ragged edges, a mushy stool. |
| Type 7 | Watery, so solid pieces. |

It is very important to apply to the patient the correct dosage regimen to achieve the therapeutic objective. Emphasis has to be placed on the route of administration, galenic formulation, unit dose, frequency of administration, loading dose and length of treatment. However there remains a need to provide a flexible dosage regimen which is adaptable depending on the change of reduction of certain indicators of CDI or CDAD or certain gut microflora indicators to secure best possible treatment for each patient and for reducing the recurrence of CDI or CDAD in said patient after the end of the treatment to a minimum level.

SUMMARY OF INVENTION

After having carried out detailed investigations, the present inventors have been able to provide one or more of a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of the tiacumicin compound twice a day; (2)

monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed. Further the invention provides the use of the tiacumicin compound to reduce recurrence in a patient suffering from CDI or CDAD as well as a process for reducing recurrence.

DESCRIPTION OF EMBODIMENTS

The present invention relates to a tiacumicin compound, a stereo-isomer thereof, a polymorph thereof or a pharmaceutically acceptable solvate thereof for use in the oral treatment of Clostridium difficile infections (CDI) or Clostridium difficile-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed.

The tiacumicin compound according to the present invention, has an 18-membered macrocyclic glycoside structure and is a compound as disclosed in U.S. Pat. Nos. 4,918,174; 5,583,115; 5,767,096; and in Chinese patent applications 201010526416.9 and 201110104051.5, herein incorporated by reference.

Preferred tiacumicin compounds are selected from the group consisting of tiacumicin A, tiacumicin B and analogues thereof, (dialkyltiacumicins and bromotiacumicins), tiacumicin C, tiacumicin D, tiacumicin E, tiacumicin F and lipiarmycin. Though all tiacumicin compounds have in common that they are insoluble or almost insoluble in water, more preferably, the active ingredient is lipiarmycin or tiacumicin B or a stereo-isomer thereof or a polymorph thereof. Even more preferred as tiacumicin compound is R-tiacumicin B (also known as fidaxomicin, OPT-80, or PAR-101).

R-tiacumicin B is also known under the name fidaxomicin (3-[[[6-deoxy-4-O-(3,5-dichloro-2-ethyl-4,6-dihydroxyben- zoyl)-2-O-methyl-β-D-mannopyranosyl]oxy] methyl]-12 (R)-[[6-deoxy-5-C-methyl-4-O-(2-methyl-1-oxopropyl)-β- D-lyxo-hexopyranosyl]oxy]-11 (S)-ethyl-8(S)-hydroxy-18 (S)-(1(R)-hydroxyethyl)-9,13,15-trimethyloxacyclooctade ca-3,5,9,13,15-pentaene-2-one or oxacyclooctadeca-3,5,9, 13,15-pentaen-2-one, 3-[[[6-deoxy-4-O-(3,5-dichloro-2-et- hyl-4,6-dihydroxybenzoyl)-2-O-methyl-β-D-mannopyrano- syl]oxy]methyl]-12-[[6-deoxy-5-C-methyl-4-O-(2-methyl- 1-oxopropyl)-β-D-lyxo-hexopyranosyl]oxy]-11-ethyl-8-hy- droxy-18-[(1R)-1-hydroxyethyl]-9,13,15-trimethyl-, (3E, 5E,8S,9E,11S,12R,13E,15E,18S)). It is a compound that has a narrow antimicrobial spectrum, with activity against Clostridium difficile and most strains of staphylococci and enterococci but negligible activity against gram-negative organisms and fungi. It is obtained by fermentation of Dactylosporangium aurantiacum and corresponds to the following formula (II):

Therefore another embodiment of the present invention relates to a tiacumicin compound, a stereo-isomer thereof, a polymorph thereof or a pharmaceutically acceptable solvate thereof for use in the oral treatment of Clostridium difficile infections (CDI) or Clostridium difficile-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed, wherein the tiacumicin compound is fidaxomicin (R-tiacumicin B).

The expression "stereo-isomer thereof" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity. The symbols "R" and "S" represent the configuration of substituents around a chiral carbon atom.

The isomeric descriptors "R" and "S" are used as described herein for indicating atom configuration relative to a core molecule and are intended to be used as defined in the literature (IUPAC Recommendations 1996, Pure & Applied Chemistry 68: 2193-2222). The expression "polymorph thereof" describes any alternative crystalline form having different physical properties as a result of the different order of the molecule in a crystal lattice. More specifically, polymorphs such as disclosed in WO2008/091554 are included. The expression "pharmaceutically acceptable solvate thereof" describes any pharmaceutically acceptable solvate that, administered to a patient (directly or indirectly) provides a tiacumicin compound. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

CDI stands for *Clostridium difficile* infections and CDAD stands for *Clostridium difficile*-associated disease or diarrhea. Both expressions have the same meaning and are interchangeable. If in the present invention reference is made to CDI it also includes CDAD and vice versa.

The expression "patient" refers to any human suffering from CDI or CDAD;

The state of disease of a *Clostridium difficile* infection can be monitored by various indicators. Suitable indicators are for example the consistency of stools, the frequency of diarrhea, the presence of *Clostridium difficile* toxin A (TcdA) or toxin B (TcdB toxin), the presence of *Clostridium difficile* toxin A (TcdA) and toxin B (TcdB toxin) together, the presence of the *Clostridium difficile* toxin B gene (tcdB) or the *Clostridium difficile* toxin A gene (tcdA), the presence of the *Clostridium difficile* toxin B gene (tcdB) and the *Clostridium difficile* toxin A gene (tcdA) together and the presence of the *Clostridium difficile* surface antigen (GDH=glutamate dehydrogenase) and possibly inflammatory biomarkers such as fecal lactoferrin (e.g. detection by Enzyme Immuno Assay (EIA) from Hycultbiotech), calprotectin (e.g. detection by Enzyme Immuno Assay (EIA) from Hycultbiotech or BIOHIT Healthcare), C-reactive protein (CRP) (e.g. detection by Enzyme Immuno Assay (EIA) from Novex), fecal IL-8 m RNA (detection by qRT-PCR; Feghaly et al., 2013:57, Clinical Infection Diseases), Fecal CXCL-5 mRNA (detection by qRT-PCR; Feghaly et al., 2013:57, Clinical Infection diseases). The various indicators can be used alone or in combination with one of the other indicators to determine the disease state of a patient.

Preferred indicators according to the present invention are selected from the group consisting of (a) Frequency of diarrhea, (b) Consistency of stool (c) *Clostridium difficile* toxin B (TcdB toxin) and/or *Clostridium difficile* toxin A (TcdA toxin), (d) *Clostridium difficile* toxin B gene (tcdB) and (e) *Clostridium difficile* surface antigen (GDH) to monitor CDI or CDAD. Each of these indicators can be used alone or in combination with one or more of the selected indicators to monitor CDI or CDAD.

The phrase "positively changed" or a "positive change" in the present invention refers to the fact that a specific indicator of CDI or CDAD is compared at the start of the treatment and during the initial course of treatment to establish if the initial course of treatment is effective for the treatment of CDI or CDAD. An effective treatment would result in an improved value of the indicator (=indicator is positively changed or a positive change of the indicator)—meaning that the value of an indicator has decreased during the initial course of treatment—which allows to switch the patient to the intermittent course of treatment. The meaning of a positive change will be explained hereinafter for each of the preferred indicators.

The phrase "favourably changed" in the present invention refers to the fact that a specific indicator of gut microflora is compared at the start of the treatment and during the intermittent course of treatment to establish if the gut microflora has recovered and the intermittent treatment can be discontinued. "Favourably changed" in the present invention means that microorganisms, which support colonisation resistance against CDI have increased in abundance (such as Bacteroidetes and Firmicutes) and microorganisms which work against colonisation resistance against CDI should be reduced in abundance (such as Proteobacteria).

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed, wherein the indicator of CDI or CDAD is selected from the group consisting of (a) Frequency of diarrhea, (b) Consistency of stool (c) *Clostridium difficile* toxin B (TcdB toxin) and/or *Clostridium difficile* toxin A (TcdA toxin), (d) *Clostridium difficile* toxin B gene (tcdB) and (e) *Clostridium difficile* surface antigen (GDH).

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the indicator of CDI or CDAD is the frequency of diarrhea.

The frequency of diarrhea or Unformed Bowel Movements (UBM) is a suitable indicator for monitoring an improvement of the symptoms of CDI or CDAD. For example the reduction of the frequency of diarrhea to less than four UBM per day for two consecutive days is a positive change of the indicator. A preferred embodiment of the present invention is the reduction of the frequency of diarrhea to less than 3 UBM per day for two consecutive days. The frequency of UBM or diarrhea will be detected by observation through patient's notes or a stool diary.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the indicator of CDI or CDAD is the consistency of the stools. An accepted model to those skilled in the art is the Bristol Stool form scale as published by S. J. Lewis et al. In *Scandinavian Journal of Gastroenterology*, 1997, Vol. 32, No. 9, pages 920-924. In table 1 of this publication the seven types of the Bristol stool form scale is defined wherein type 7 is a watery stool and type 1 are separate hard lumps. In the present invention a positive change of the indicator is a change of stool consistency from type 7 or 6 to type 4 or to a type below 4 according to the Bristol stool form scale. A preferred embodiment of the present invention is, wherein the consistency of the stool shows an improvement from type 7 or 6 to type 4 of the Bristol stool form scale.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the indicator of CDI or CDAD is the *Clostridium difficile* toxin B (TcdB toxin). During infection, *Clostridium difficile* produces two key virulence determinants, toxin A (TcdA) and toxin B (TcdB). Toxin B and toxin A (TcdA) are therefore key indicators for CDI. To establish, if the initial course of treatment of the dosage regime of the present invention is effective for the treatment of CDI or CDAD, the TcdB toxin and/or the TcdA toxin should be either negative in a qualitative test or if a quantitative assay is used the level of TcdB toxin and/or TcdA toxin should be below the lower limit of detection (LLOD). A preferred embodiment of the present invention is the tiacumicin compound for use, wherein the *Clostridium difficile* toxin B (TcdB toxin) is absent. The presence of TcdA and/or TcdB can be determined by an Enzyme-Linked Immuno SorbentAssay (ELISA) or an Enzyme Immuno Assay (EIA). ELISA and EIA are exchangeable expressions. Suitable EIA assays to determine the absence of CDI are *Clostridium difficile* TOX A/B II test (from TechLab) or *Clostridium difficile* TOX-B test (from TechLab).

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the indicator of CDI or CDAD is the *Clostridium difficile* toxin B gene (tcdB) or *Clostridium difficile* toxin A gene (tcdA) To establish, if the initial course of treatment of the dosage regimen of the present invention is effective for treatment of CDI or CDAD, the tcdB and/or tcdA should be absent if tested with nucleic acid amplification technology or if a quantitative assay is used the level of tcdB and/or tcdA should be below the lower limit of detection (LLOD). A preferred embodiment of the present invention relates to the tiacumicin compound for use, wherein the tcdB is absent. Suitable assays for determining the absence of tcdA and/or tcdB are Xpert *C. Difficile* assay from Cepheid.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the indicator of CDI or CDAD is the *Clostridium difficile* surface antigen (GDH=Glutamate dehydrogenase). To establish, if the initial course of treatment of the dosage regimen of the present invention is effective for treating CDI or CDAD, the GDH toxin should be either absent in a qualitative test or if a quantitative assay is used the level of GDH should be below the lower limit of detection (LLOD). A preferred embodiment of the present invention relates to the tiacumicin compound for use, wherein the GDH is absent. A suitable assay for determining the absence of GDH is for example an EIA called *Clostridium difficile* CHEK 60 from TechLab.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidoxomicin every other day if the one or the more of the indicators of CDI or CDAD are positively changed, wherein the frequency of diarrhea is reduced to less than 4 unformed bowel movements (UBM) per day for two consecutive days.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidoxomicin every other day if the one or the more of the indicators of CDI or CDAD are positively changed, wherein the consistency of the stool shows an improvement from type 7 or type 6 to type 4 according to the Bristol stool form scale.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidoxomicin every other day if the one or the more of the indicators of CDI or CDAD are positively changed, wherein the *Clostridium difficile* toxin B (TcdB) and the *Clostridium difficile* toxin A (TcdA) are absent.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or more of the indicators; and (4) switching to an intermittent course of treatment by administering to the patient 200 mg of fidaxomicin every other day if the one or the more of the indicators of CDI or CDAD are positively changed, wherein the *Clostridium difficile* toxin B (TcdB) is absent.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidaxomicin every other day if the one or the more of the indicators of CDI or CDAD are positively changed, wherein the *Clostridium difficile* toxin B gene (tcdB) is absent Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to the following dosage regimen: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidaxomicin every other day if the one or the more of the indicators of CDI or CDAD are positively changed, wherein the *Clostridium difficile* surface antigen (GDH) is absent.

Suitable indicators for monitoring the recovery from CDI or CDAD could be also urinary metabolic biomarkers such as the decrease of urinary metabolites associated with enterobacteriaceae and/or the increase of urinary metabolites (such as hippurate, 4-cresol sulphate) associated with obligate anaerobes in the urine.

The phrase "initial course of treatment" refers to a dosage regimen (or the portion of a dosage regimen) that is used for the initial treatment of a disease. In a preferred embodiment of the present invention the initial course of treatment lasts for 3 to 10 days, even more preferred 5 days.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, further comprising a resting of period between 1 and 10 days before the intermittent course of treatment.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, further comprising a resting of period between 4 and 6 days before the intermittent course of treatment.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, further comprising a resting of period of 5 days before the intermittent course of treatment.

Another embodiment of the present invention relates to the tiacumicin compound, the stereo-isomer thereof, the polymorph thereof or the pharmaceutically acceptable solvate thereof for use in the oral treatment of *Clostridium difficile* infections (CDI) or *Clostridium difficile*-associated disease (CDAD) in a patient according to the dosage regimen, wherein the intermittent course of treatment lasts between 4 and 40 days, preferably between 10-30 days, even more preferred for 20 days.

Gut microflora composition of healthy individuals varies depending on circumstances such as food, age and geography, nevertheless certain microorganism are commonly found in healthy individuals such as Firmicutes (includes major Gram positive anaerobes including Clostridia groups XIVa and IV, Lachnospiraceae, Ruminococcaceae as well as minor facultative anaerobes such as Enterococci and Lactobacilli) and Bacteroidetes (includes major Gram negative anaerobes e.g. *Bacteroides* and *Prevotella*), as well as smaller groups such as the Actinobacteria (which includes the Bifidobacteria family) and Proteobacteria such as Enterobacteriaceae.

The above mentioned gut flora microorganisms can be seen as indicators of gut microflora recovery and guarantee at the right levels a colonisation resistance against CDI. To achieve gut microflora recovery the abundance of Bacteroides and Firmicutes must be increased and the abundance of Proteobacteria reduced. It is important to achieve the right balance between anaerobes, such as *Bacteroides* and Firmicutes, and Proteobacteria such as Enterobacteriaceae.

Yet another embodiment of the present invention relates to the intermittent course of treatment of the claimed dosage regimen, wherein the intermittent course of treatment will be discontinued when certain indicators, known for gut microflora recovery, have favourably changed.

Therefore another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; (4) switching to an intermittent course of treatment by administering to the patient 200 mg of the tiacumicin compound every other day if the one or the more of the indicators of CDI or CDAD are positively changed; (5) monitoring one or more indicators of gut microflora; and (6) discontinuing the intermittent course of treatment if the one or the more of the indicators of gut microflora have favourably changed.

A suitable indicator for gut microflora is the Enterobacteriaceae count. The Enterobacteriaceae belong to the Proteobacteria family. A preferred embodiment of the present invention is, wherein the Enterobacteriaceae count is reduced to at least 90% compared to the level before the initial course of treatment. The Enterobacteriaceae are a large family of Gram-negative bacteria that includes, along with many harmless symbionts, many of the more familiar pathogens, such as *Salmonella, Escherichia coli, Yersinia pestis, Klebsiella* and *Shigella*. Other disease-causing bacteria in this family include *Proteus, Enterobacter, Serratia*, and *Citrobacter*. A reduction of the Enterobacteriaceae count to at least 90% compared to the Enterobacteriaceae count before the initial treatment is indicative of return to a normal functioning intestine and will indicate when to stop therapy.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of fidaxomicin every other day if the one or the more of the indicators of CDI or CDAD are positively changed; (5) monitoring one or more indicators of gut microflora; and (6) discontinuing the intermittent course of treatment if the one or the more of the indicators of gut microflora have favourably changed., wherein the total *Enterobacteriaceae* count of gut microflora is 90% reduced compared to the level prior to the initial course of treatment.

A preferred embodiment of the present invention relates to the intermittent course of treatment of the claimed dosage regimen, wherein the intermittent course of treatment will be discontinued when the level of *Bacteroides* and Firmicutes is at 80% of baseline level. Another preferred embodiment of the present invention relates to the intermittent course of treatment of the claimed dosage regimen, wherein the intermittent course of treatment will be discontinued when a balance of anaerobes (*Bacteroides* and Firmicutes) and protobacteria is achieved.

Along with its narrow antimicrobial spectrum, fidaxomicin also has a prolonged postantibiotic effect against *Clostridium difficile*. Besides the obvious benefit to the patient, the prevention of recurrence would eliminate the costs of treating additional episodes of *Clostridium difficile* infection and should reduce the rate of person-to-person transmission.

This is an effective treatment for CDI, and is associated with reduced rates of recurrence as compared with vancomycin. However, these existing dosing regimens were not optimised for recovery of microflora but chosen based on existing practice for vancomycin and metronidazole. However, both vancomycin and metronidazole disrupt microflora and so recovery cannot start until after treatment has been removed.

The impact of the new dosage regimen on recurrence of CDI is an important factor for the present invention. Also import is the impact of the new dosage regimen on refractory CDI.

From earlier published Phase 3 trials, the non-inferiority of clinical cure after 10 days in patients with CDI for orally administered fidaxomicin compared to orally administered vancomycin, and the superiority shown for the secondary endpoints recurrence rate and sustained cure rate within 30 days after discontinuation of treatment are considered highly clinically relevant.

Nevertheless, despite the significant reduction in recurrence from 26% for vancomycin to 14.1% (mITT analysis=Modified Intention to Treat Population analysis) for fidaxomicin in the Phase III studies, recurrence of CDI remains the major unmet medical need in this disease area, resulting in significant morbidity and mortality for patients in addition to wider societal and health care system costs.

The new dosage regimen of the present invention reduces the recurrence to less than 10% 30 days after end of the treatment, preferably to less than 5% 30 days after end of the treatment and even more preferred to less than 3% 30 days after end of the treatment.

Another embodiment of the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile*-associated disease (CDAD) in a patient according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed, wherein the recurrence of CDI or CDAD in a patient is less than 10% 30 days after end of treatment. In a preferred embodiment the recurrence in a patient is less than 5% 30 days after end of the treatment and in an even more preferred embodiment the recurrence is less than 3% 30 days after end of the treatment.

Another embodiment of the present invention relates to the use of a tiacumicin compound, a stereo-isomer thereof, a polymorph thereof or a pharmaceutically acceptable solvate thereof in the oral treatment of a patient suffering from CDI or CDAD to reduce recurrence of CDI or CDAD in such a patient to less than 10% 30 days after end of treatment according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed.

Another embodiment of the present invention relates to the use of a tiacumicin compound, a stereo-isomer thereof, a polymorph thereof or a pharmaceutically acceptable solvate thereof in the oral treatment of a patient suffering from CDI or CDAD to reduce the recurrence of CDI or CDAD in such a patient to less than 10% 30 days after end of treatment according to a dosage regimen comprising: (1) administering to the patient in an initial course of treatment 200 mg of fidaxomicin twice a day; (2) monitoring the efficacy of the initial course of treatment in the patient by means of monitoring changes of one or more indicators of CDI or CDAD; (3) assessing whether there is a positive change of the one or more of the indicators; and (4) switching to an intermittent course of treatment by administering to the patient 200 mg of fidaxomicin every other day if the one or the more of the indicators of CDI or CDAD are positively changed.

Another embodiment of the present invention relates to the use of a tiacumicin compound, a stereo-isomer thereof, a polymorph thereof or a pharmaceutically acceptable solvate thereof in the oral treatment of a patient suffering from CDI or CDAD to reduce the recurrence of CDI or CDAD in such a patient to less than 10% 30 days after end of treatment according to the dosage regimen, wherein the indicator of CDI or CDAD is selected from the group consisting of (a) Frequency of diarrhea, (b) Consistency of stool (c) *Clostridium difficile* toxin B (TcdB toxin) and/or *Clostridium difficile* toxin A (TcdA toxin), (d) *Clostridium difficile* toxin B gene (tcdB) and (e) *Clostridium difficile* surface antigen (GDH).

Another embodiment relates to a method of treating *Clostridium difficile* infections (CDI) or *Clostridium difficile*-associated disease (CDAD) in a patient comprising: (1) administering to the patient 200 mg of a tiacumicin compound twice a day as initial course of treatment; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day if the one or the more of the indicators of CDI or CDAD are positively changed.

Another embodiment of the present invention relates to the method of treating CDI or CDAD in a patient, wherein the tiacumicin compound is fidaxomicin (R-tiacumicin B).

Another embodiment of the present invention relates to the method of treating CDI or CDAD in a patient, wherein the indicator of CDI or CDAD is selected from the group consisting of (a) Frequency of diarrhea, (b) Consistency of stool (c) *Clostridium difficile* toxin B (TcdB toxin) and/or *Clostridium difficile* toxin A (TcdA toxin), (d) *Clostridium difficile* toxin B gene (tcdB) and (e) *Clostridium difficile* surface antigen (GDH).

Another embodiment of the present invention relates to the method of treating CDI or CDAD in a patient, wherein the indicator of CDI or CDAD is the frequency of diarrhea.

Another embodiment of the present invention relates to the method of treating CDI or CDAD in a patient, wherein the frequency of diarrhea is reduced to less than 4 unformed bowel movements (UBM) per day for 2 consecutive days.

Another embodiment of the present invention relates to the method of treating CDI or CDAD in a patient, wherein the indicator of CDI or CDAD is the consistency of the stool.

Another embodiment of the present invention relates to the method of treating CDI or CDAD in a patient, wherein the consistency of the stool shows an improvement from type 7 or type 6 to type 4 according to the Bristol stool from scale.

Another embodiment of the present invention relates to the method of treating CDI or CDAD in a patient, wherein the indicator of CDI or CDAD is *Clostridium difficile* toxin B(TcdB).

Another embodiment of the present invention relates to the method of treating CDI or CDAD in a patient, wherein the *Clostridium difficile* toxin B (TcdB) is absent.

The compositions to be used in the dosage regimen according to the invention may be a pharmaceutical composition. Another embodiment of the present invention is a pharmaceutical composition comprising a tiacumicin, a stereo-isomer thereof, a polymorph thereof or a pharmaceutically acceptable solvate thereof for use in the oral treatment of a patient suffering from CDI or CDAD and is therefore orally administered in an initial course of treatment 200 mg of a tiacumicin compound twice a day and is evaluated by means of monitoring the efficacy of the initial course of treatment in the patient and changes of one or more indicators of CDI or CDAD, which method comprises an intermittent course of treatment by administering to the patient 200 mg of a tiacumicin compound every other day once the one or the more of the indicators have positively changed.

The compositions to be used in the dosage regimen according to the invention may be an aqueous suspension, a dry powder for an aqueous suspension, a dry granulate for an aqueous suspension or a dispersible tablet, a capsule, a tablet, optionally film-coated. A preferred composition for oral administration is a tablet, in particular a film-coated tablet.

The term tablet also comprises fast-disintegrating tablets, amongst which are dispersible tablets and effervescent tablets.

The most commonly used methods of tablet preparation are direct compression, dry granulation and wet granulation. Direct compression involves compressing a mixture containing the active ingredient(s) and the excipient(s) on a tablet press (L. Lachman et al., in: The Theory and Practice of Industrial Pharmacy, 3rd ed., 1986). The mixture to be compressed must possess both good flow and compression properties in order to produce tablets having a uniform content of the active ingredient(s). Good flow properties cannot always be achieved by adding appropriate excipients, such as lubricants, anti-adhesive agents and flow-promoters to the mixture. Hence frequently the mixture is granulated prior to compression.

Granulation is a process by which sphere-like or regularly shaped aggregates called granules are formed out of the powder mixture. This can be achieved by dry granulation methods and wet granulation methods.

Granulation is also used for converting a mixture of powders with poor cohesion into aggregates, which when compressed result in tablets that have good cohesion properties.

In the case of fast-disintegrating tablets, the active ingredient(s), optionally in admixture with one or more excipients, is (are) advantageously provided with a coating in order to mask the taste of such ingredient(s) and/or to protect the same against possible harmful effects by light and/or moisture and in the case of bendamustine to protect the mucosa in the mouth against the harmful effects exerted by the active compound. For that purpose a granulate preferably is prepared and processed as further outlined below.

The expression "granulate" refers to aggregates of particles, sometimes called granules. A granulate in general is prepared by compaction and/or compression techniques (dry granulation) or by wet granulation techniques, using a liquid in which optionally a wet granulation binding agent is dissolved (Remington's Pharmaceutical Sciences 18th ed. 1990, page 1641). Wet granulation techniques also include extrusion techniques.

Accordingly the term granulate also comprises pellets, spherules, and extrudates, of which pellets preferably are used as examples of a granulate.

A pellet may be described as a small particle of approximately 1.0-1.6 mm in diameter and having a certain density, which particle is prepared by application of the pharmaceutical processes of extrusion and spheronisation to powder mixtures.

The active ingredient(s), optionally in admixture with one or more excipients, may be advantageously provided with a coating in order to mask the taste of such ingredient and/or to protect the same against possible harmful effects by light and/or moisture and/or to protect the mucosa in the mouth against the harmful effects exerted by the active compound.

Preferably the dosage forms to be used in accordance with the dosage regimens according to the invention are prepared by dry compaction techniques. Suitable techniques are for example described in Remington's Pharmaceutical Science 18th. ed. 1990, page 1644. They comprise dry granulation, roller compaction and direct compression. When tablets are prepared by these techniques, it is even more advantageous to use direct compression.

The dosage forms to be used in accordance with the treatment regimen according to the present invention are preferably provided with a coating.

The coating has different purposes: it may serve for masking the taste of the active ingredient(s) used in the composition, whilst at the same time it is protecting the active ingredient against possible harmful effects by light and/or moisture such as oxidation, degradation, etc. Furthermore, the coating layer may prevent the subject from damage of the oral mucosa by the active ingredient.

The coating layer can be applied to the dosage forms by techniques well-known in the art such as spray-coating and microencapsulation. For tablets it can be in the form of a film-coating, a saccharide-coating or a compression coating. Preferably a film-coating process is used (Remington's Pharmaceutical Sciences 18th ed. 1990, page 1666). In case an active ingredient requires the application of a coating for fast-disintegrating tablets the individual granules can suitably be provided with a coating prior to compression into tablets.

Preferably it also contains a filler or diluents agent. Examples of such suitable compounds are:
- sugars, which may be selected from the group consisting of sucrose, fructose, sorbitol, xylitol, maltitol, aspartame, erythritol, isomalt, trehalose, maltose, mannose, sorbose, xylose, dextran, dextrin, pullulan, mannitol and lactose;
- microcrystalline cellulose or microfine cellulose;
- starch, a soluble starch or a starch derivative, such as a hydroxyethyl starch;
- calcium carbonate, sodium chloride, calcium phosphate, calcium hydrogen phosphate, calcium sulfate, sodium phosphate, carmellose potassium, carmellose calcium, carmellose sodium, synthetic aluminum silicate, etc.

Most preferred are microcrystalline cellulose and a sugar, selected from the group consisting of D-mannitol, erythritol, isomalt and trehalose. However, there is a preference for the use of microcrystalline cellulose, in view of stability of the composition containing fidaxomicin and xanthan gum, under a variety of storage conditions. On top of that for certain groups of patients who should not take sugar-containing compositions, the use of microcrystalline cellulose is advantageous.

The amount of microcrystalline cellulose should be as low as possible, but does not seem to be critical. The same is true when a sugar is used.

The granulate may further contain one or more of a disintegrant, since it is important that the fidaxomicin is quickly and uniformly dispersed, both in in vitro and in vivo situations. Suitable disintegrating agents are corn starch, potato starch, partly pregelatinized starch, but also the so-called super-disintegrants can be used; examples of which are crosscarmellose calcium, crosscarmellose sodium, crospovidone, sodium starch glycolate, low-substituted hydroxypropylcellulose and Amberlite IRP 88. A preferred disintegrant is sodium starch glycolate, which is commercially available under the trademark Primojel®. This disintegrant has shown that it is effective in compositions which contain either microcrystalline cellulose or a sugar as the diluents. Further it has shown that it contributes to an easy manufacturing of a granulate composition. Optionally a second disintegrant can be used, such as partly pregelatinised starch.

The composition to be used in accordance with the treatment regimen according to the invention can be an aqueous suspension, preferably in admixture with excipients, such as buffering agents, preservatives, flavouring agents, sweetening agents and viscosity increasing agents. Most preferably the compositions contain flavouring and sweetening agents to mask the taste of the tiacumicin compounds.

Examples of buffering agents are hydrochloric acid, diluted hydrochloric acid, sulfuric acid, adipic acid and its salt, citric acid and its salt, gluconic acid and its salt, succinic acid and its salt, ascorbic acid and its salt, glacial acetic acid and its salt, acetic acid and its salt, tartaric acid and its salt, fumaric acid and its salt, maleic acid and its salt, lactic acid and its salt, malic acid and its salt, phosphoric acid, and its salt, glycine, sodium hydrogencarbonate, sodium carbonate, sodium hydroxide, magnesium hydroxide etc. and combinations of the afore-mentioned agents.

Examples of preservatives are benzoic acid and its salt, an edetate acid and its salt, salicylic acid and its salt, dibutyl-hydroxytoluene, sorbic acid and its salt, a sodium dehydroacetate, para-hydroxybenzoic acid, and its salt, methylparaben, propylparaben, etc. and combinations of the afore-mentioned preservatives.

Examples of flavouring agents are orange essence, an orange oil, caramel, camphor, cinnamon oil, a spearmint oil, strawberry essence, chocolate essence, a cherry flavor, oil of bitter orange, pine|pineapple oil, mentha oil, a vanilla flavor, bitter essence, a fruits flavor, peppermint essence, a mix flavor, a mint flavor, menthol, lemon powder, a lemon oil, a rose oil etc. and combinations of the afore-mentioned flavouring agents.

Examples of sweetening agents are sucralose, aspartame, fructose, xylitol, glycyrrhizinic acid and its salt, saccharin and its salt, stevia, sucrose, sorbitol, glucose, hydrogenated maltose starch syrup, maltitol, maltose, etc. and combinations of the afore-mentioned sweetening agents.

Examples of viscosity enhancing agents are celluloses such as methylcellulose, ethylcellulose, hydroxypropylcellulose, hydroxyethylcellulose, hydroxypropylmethylcellulose, carboxymethylcellulose; gums such as xanthan gum, guar gum, gellan gum, dextran, carrageenan; polyvinylpyrrolidone; specially treated microcrystalline celluloses, such as water dispersible celluloses (microcrystalline cellulose and sodium carboxymethylcellulose); and combinations of the afore-mentioned viscosity enhancing agents.

Alternatively, the granulate to be used in accordance with the treatment regimen according to the invention in admixture with extragranular excipients can be used for the preparation of dispersible tablets.

The tiacumicin compounds of the present invention may be used in combination with other active ingredients. For example more than one tiacumicin compound may be combined for the oral treatment of CDI or CDAD. Polyclonal and monoclonal antibodies have shown positive effects in the treatment of CDI or CDAD. Polyclonal antibodies for example facilitate treatment in patients. Recent clinical trials have demonstrated that monoclonal antibodies in combination with antibiotic therapy are able to reduce the recurrence of CDI in patients (Simon et al, Polyclonal antibody Therapies for *Clostridium difficile* Infection, Antibodies 2014, 3, 272-288). Therefore a useful combination may be Fidaxomicin in combination with monoclonal or polyclonal antibodies. Especially useful monoclonal antibodies to be combined with Fidaxomicin are those, which may reduce TcdA and TcdB mediated TNF-α and IL-1β expression.

The following examples further illustrate the invention. It will be apparent to the skilled person that these examples are solely for illustrative purposes and must not be considered to limit the invention.

EXAMPLE 1

A Phase IIIb/IV randomized, controlled, open-label, parallel group study to compare the efficacy of vancomycin therapy to the intermittent dosage regimen of fidaxomicin therapy (Extended Fidaxomicin (FDX) study, also called EXTEND having the study number 2819-MA-1002) in the sustained clinical cure of *Clostridium difficile* infection in an older population is performed.

The objective of the study is to evaluate whether the fidaxomicin intermittent dosage regimen therapy is superior to the standard vancomycin therapy in sustained clinical cure of CDI at 30 days after end of treatment (Day 40 or Day 55) and to compare recurrence of CDI at day 40, day 55 and day 90.

Table 1 shows one possible intermittent dosage regimen according to the present invention.

Dose Rationale

Fidaxomicin (FDX) is believed to reduce recurrence primarily through minimal collateral damage to colonic microflora. The approved dosing regimen for FDX (200 mg q12 hr for 10 days) was not optimised for recovery of microflora but chosen based on existing practise for vancomycin and metronidazole. Hence the study dosing of fidaxomicin (Dificlir™) to be administered is not in line with the current approved SmPC for Dificlir™ and has been selected with a view to maximizing the attributes of this product in treating CDI. Subjects will receive 200 mg twice daily (b.i.d.) for 5 days from Day 1 to Day 5. From Day 6 to Day 25, subjects will receive 200 mg once daily on alternate days (first alternate day dose given on Day 7). This extension of the dose will allow a longer period for the protective microflora to recover and extend the period of time over which *Clostridium difficile* cells are suppressed, and kill any dormant spores that germinate. The extension of the dose also targets the early recurrence period documented in the phase 3 studies—the first 15 days after the end of therapy during which the majority of recurrences occurred. By covering this period this revised dosing regimen may reduce the recurrence to <10%, preferably to <5% and even more preferred to <3%. The impact on the gut microflora was limited supporting the rationale for this study.

The dosing of vancomycin (Vancocin™) to be administered in this study is in line with the SmPC for Vancocin. Subjects will receive 125 mg four times daily (q.i.d.) for 10 days from Day 1 to Day 10.

EXAMPLE 2

Results of the Phase IIb/IV Study as Described in Example 1

A Phase IIIb/IV randomized, controlled, open-label, parallel group study to compare the efficacy of standard vancomycin (VAN) therapy to that of the extended dosage regimen of Fidaxomicin therapy (Extended Fidaxomicin (FDX) study, also called EXTEND having the study number 2819-MA-1002) in the sustained clinical cure of *Clostridium difficile* infection in an older population was performed. The dosage regimen was as described in Table 1 of Example 1.

Table 2 shows the summary of demographic and baseline characteristics

| | | Day | | | | | | | | | | | | | | | | | | | | | | | | |
|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
| Vancomycin | am | V | V | V | V | V | V | V | V | V | V | | | | | | | | | | | | | | | |
| | | V | V | V | V | V | V | V | V | V | V | | | | | | | | | | | | | | | |
| | pm | V | V | V | V | V | V | V | V | V | V | | | | | | | | | | | | | | | |
| | | V | V | V | V | V | V | V | V | V | V | | | | | | | | | | | | | | | |
| Fidaxomicin | am | F | F | F | F | F | | F | | F | | F | | F | | F | | F | | F | | F | | F | | F |
| | pm | F | F | F | F | F | | | | | | | | | | | | | | | | | | | | |

F = fidaxomicin 200 mg oral tablets
V = vancomycin 125 mg oral capsules

| Parameter | Extended FDX (N = 181) | Standard VAN (N = 181) | Total (N = 362) |
|---|---|---|---|
| Sex | | | |
| Male | 72 (39.8%) | 79 (43.6%) | 151 (41.7%) |
| Female | 109 (60.2%) | 102 (56.4%) | 211 (58.3%) |
| Age (mean ± SD) in years | | | |
| Mean | 75.2 ± 8.4 | 74.9 ± 8.9 | 75.1 ± 8.6 |
| Min. | 60 | 60 | 60 |
| Max. | 94 | 95 | 95 |
| Age group (years) | | | |
| <75 | 83 (45.9%) | 82 (45.3%) | 165 (45.6%) |
| ≥75 | 98 (54.1%) | 99 (54.7%) | 197 (54.4%) |
| BMI (mean ± SD) in kg/m$^2$ | 25.29 ± 4.28 | 24.93 ± 5.27 | 25.11 ± 4.80 |
| CDI severity at baseline | | | |
| Severe | 93 (51.4%) | 100 (55.2%) | 193 (53.3%) |
| Non-severe | 88 (48.6%) | 81 (44.8%) | 169 (46.7%) |
| Number of previous recurrences in the last three months prior to randomization | | | |
| 0 | 143 (79.0%) | 142 (78.5%) | 285 (78.7%) |
| 1 | 28 (15.5%) | 26 (14.4%) | 54 (14.9%) |
| 2 | 10 (5.5%) | 13 (7.2%) | 23 (6.4%) |
| Number of Unformed Bowel Movements (UBM) in the last 24 hours prior to randomization | | | |
| n | 178 | 179 | 357 |
| Mean ± SD | 6.7 ± 4.73 | 6.3 ± 3.36 | 6.5 ± 4.10 |
| Median (min, max) | 5.0 (2, 50) | 5.0 (3, 20) | 5.0 (2, 50) |
| Use of antibiotics for conditions other than CDI prior to the study | | | |
| Yes | 132 (72.9%) | 130 (71.8%) | 262 (72.4%) |
| No | 49 (27.1%) | 51 (28.2%) | 100 (27.6%) |
| Use of anti-diarrhea medication in the last 24 hours prior to randomization | | | |
| Yes | 41 (22.7%) | 39 (21.5%) | 80 (22.1%) |
| No | 140 (77.3%) | 142 (78.5%) | 282 (77.9%) |
| Charlson Co-Morbidity Index Score | | | |
| Mean | 7.1 ± 2.69 | 7.3 ± 2.53 | 7.2 ± 2.61 |

The distribution of the demographic and baseline characteristics are similar between the two treatment groups. The proportion of patients with 0, 1 and 2 previous recurrences of CDI in the combined group is 78.7%, 14.9% and 6.4% respectively. The average number of unformed bowel movements in the last 24 hours before randomization is approximately 6.5 (±4.10 SD).

TABLE 3

Summary of sustained clinical cure at 30 days after end of treatment

| Parameter/Statistic | Extended fidaxomicin (Day 55) (N = 143) | Standard vancomycin (Day 40) (N = 167) |
|---|---|---|
| Sustained clinical cure (%) | 124/143 (86.7) | 105/167 (62.9) |
| 95% CI (CI = Confidence Interval) | (81.1, 92.3) | (55.5, 70.2) |
| Treatment Difference (95% CI) [1] | 23.8 (14.6, 33.0) | |
| p-value [2] | <0.001 | |
| OR (OR = Odds Ratio) vs. Vancomycin and 95% CI [3] | 3.36 (1.88, 5.99) | |

Sustained clinical cure is defined as clinical response as determined by Investigator at Test of Cure and no recurrence of CDI from Test of Cure until time of assessment.
[1] Difference between the rates (Extended Fidaxomicin − Standard Vancomycin) and the associated 95% confidence interval around the difference.
[2] P-value from the Cochran-Mantel-Haenszel test (general association) adjusted for the randomization factors (CDI severity [severe or non-severe], presence or absence of cancer, age [≥75 years or <75 years] and number of previous recurrences [0, 1, 2]).
[3] Estimate of the common Odds Ratio (OR) and 95% confidence interval.

TABLE 4

Recurrence of CDI at visit 5 (Day 55)

| Parameter/Statistic | Extended fidaxomicin (N = 143) | Standard vancomycin (N = 167) |
|---|---|---|
| Recurrence of CDI (%) | 5/142 (3.5) | 26/161 (16.1) |
| 95% CI (CI = Confidence Interval) | (0.5, 6.6) | (10.5, 21.8) |
| Treatment Difference (95% CI) [1] | −12.6 (−19.1, −6.2) | |
| p-value [2] | 0.001 | |
| OR (OR = Odds Ratio) vs. Vancomycin and 95% CI [3] | 0.21 (0.08, 0.58) | |

Recurrence of CDI is defined, for subjects with clinical response at Test of Cure, as re-establishment of diarrhea after Test of Cure to an extent that is greater than the frequency recorded on Day 10 for vancomycin arm or Day 25 for fidaxomicin arm, confirmed by a CDI test positive for Toxin A/B and requiring further CDI therapy.
[1] Difference between the rates (Extended fidaxomicin − Standard vancomycin) and the associated 95% confidence interval around the difference.
[2] P-value from the Cochran-Mantel-Haenszel test (general association) adjusted for the randomization factors (CDI severity [severe or non-severe], presence or absence of cancer, age [≥75 years or <75 years] and number of previous recurrences [0, 1, 2]).
[3] Estimate of the common Odds Ratio (OR) and 95% confidence interval.

In the extended FDX group, 86.7% subjects achieved sustained clinical cure at 30 days after EOT compared with 62.9% in the standard VAN group (a difference of 23.8%). At day 55, the CDI recurrence rate was 3.5% in the extended FDX arm compared with 16.1% (15/94) in the VAN arm (a difference of −12.6%).

TABLE 5

Number of Unformed bowel movements per day (UBM) in % of patients

| Day | UBM | Extended fidaxomicin | TD | Standard vancomycin | TD |
|---|---|---|---|---|---|
| −1 | <3 | 0 | — | 0 | — |
| | ≥3 | 100% | | 100% | |
| 1 | <3 | 23% | ✓ | 21.1% | ✓ |
| | ≥3 | 77.0% | | 78.9% | |
| 2 | <3 | 33.8% | ✓ | 40.6% | ✓ |
| | ≥3 | 66.2% | | 59.4% | |
| 3 | <3 | 59% | ✓ | 59.6% | ✓ |
| | ≥3 | 41% | | 40.4% | |
| 4 | <3 | 66.9% | ✓ | 72.0% | ✓ |
| | ≥3 | 33.1% | | 28.0% | |
| 5 | <3 | 73.9% | ✓ | 81.4% | ✓ |
| | ≥3 | 26.1% | | 18.6% | |
| 6 | <3 | 73.9% | — | 80.6% | ✓ |
| | ≥3 | 26.1% | | 19.4% | |
| 7 | <3 | 84.8% | ✓ | 85.5% | ✓ |
| | ≥3 | 15.2% | | 14.5% | |
| 8 | <3 | 89.1% | — | 86.8% | ✓ |
| | ≥3 | 10.9% | | 13.2% | |
| 9 | <3 | 91.3% | ✓ | 88.1% | ✓ |
| | ≥3 | 8.7% | | 11.9% | |
| 10 | <3 | 92.6% | — | 89.9% | ✓ |
| | ≥3 | 7.4% | | 10.1% | |
| 11 | <3 | 93.3% | ✓ | 91.5% | — |
| | ≥3 | 6.7% | | 8.5% | |
| 12 | <3 | 94.8% | — | 94.7% | — |
| | ≥3 | 5.2% | | 5.3% | |
| 13 | <3 | 93.3% | ✓ | 84.4% | — |
| | ≥3 | 6.7% | | 15.6% | |
| 14 | <3 | 95.6% | — | | |
| | ≥3 | 4.4% | | | |
| 15 | <3 | 94.8% | ✓ | | — |
| | ≥3 | 5.2% | | | |
| 16 | <3 | 95.5% | — | | |
| | ≥3 | 4.5% | | | |
| 17 | <3 | 95.5% | ✓ | | |
| | ≥3 | 4.5% | | | |
| 18 | <3 | 94.0% | — | | |
| | ≥3 | 6.0% | | | |
| 19 | <3 | 95.5% | ✓ | | |
| | ≥3 | 4.5% | | | |
| 20 | <3 | 97.8% | — | | |
| | ≥3 | 2.2% | | | |
| 21 | <3 | 95.5% | ✓ | | |
| | ≥3 | 4.5% | | | |
| 22 | <3 | 96.3% | — | | |
| | ≥3 | 3.7% | | | |
| 23 | <3 | 95.5% | ✓ | | |
| | ≥3 | 4.5% | | | |
| 24 | <3 | 96.2% | — | | |
| | ≥3 | 3.8% | | | |
| 25 | <3 | 96.2% | ✓ | | |
| | ≥3 | 3.8% | | | |
| 26 | <3 | 97.3% | — | | |
| | ≥3 | 2.7% | | | |
| 27 | <3 | 98.5% | — | | |
| | ≥3 | 1.5% | | | |

*TD = Treatment day

EXAMPLE 3

Detection of *Clostridium Difficile* Toxins in Human Faecal Samples

The detection of *Clostridium difficile* (*C. diff*) toxins A and B in human faecal samples was performed by ELISA. The samples to be analysed originated from clinical study 2819-MA-1002 (EXTEND). The objective of EXTEND was to investigate whether the extended fidaxomicin therapy is superior to the standard vancomycin therapy in sustained clinical cure of *Clostridium difficile* Infection (CDI) at 30 days after the end of treatment (Day 40 or Day 55) in subjects that are ≥60 years of age.

The samples were sent to LGC (Analytical lab in Fordham, Cambridgeshire, UK) packed in dry ice and upon receipt stored in a freezer (nominally −80° C.). For each patient a stool sample was collected at Day 0 (screening) and also in case of disease recurrence or an unscheduled visit. For subjects participating in the Microbiome sub-study stool samples were collected at: Day 0 (screening), Day 5, Day 12, Day 27, Day 40, Day 55 and in the case of disease recurrence or an unscheduled visit. A total of 596 faecal samples were collected during the study.

Materials

*C. difficile* toxins A and B in human faecal samples were detected using TECHLAB *C. difficile* Tox A/B II ELISA kits (Product Number T5015).

All data collection, processing (statistics) and storage was performed using the general data reduction software package, PHERAstar FS reader control software and MARS data analysis software 2.10 (BMG Labtech, version 3.10), Watson™ v7.2 and Microsoft® Excel (version 2010).

The assay readout is the spectrophotometric dual wavelength optical density (OD) read at 450 nm and referenced at 620 nm and expressed in Absorbance Units (AU). All samples were measured in duplicate. The presence (+) or absence (−) of toxin was reported together with the mean OD.

The acceptability of each batch of test samples was dependent on the data from the QC samples fulfilling the acceptance criteria outlined below in Table 5, in that all positive QCs remain above the cut off value of >0.080 OD and negative QCs remain ≤0.080 OD. All batches contained 2 separate sets of QC samples which were measured in duplicate. The precision was calculated between the OD of replicates of each set using the coefficient of variation (CV) which should be <20%.

TABLE 5

Kit acceptance criteria and assay performance limitations

| Criteria | Specification/Limits |
| --- | --- |
| Positive Control | ≥0.500 |
| Negative Control | ≤0.080 |
| Cut-off control | 0.080 |
| Toxin A Detection Level | ≥0.8 ng/mL |
| Toxin B Detection Level | ≥2.5 ng/mL |

EXAMPLE 4

Molecular Characterisation of *Clostridium difficile* Positive Human Faecal Samples LGC was appointed as the designated Central Testing Laboratory for the Molecular characterisation of *Clostridium difficile* positive stool samples in support of a Clinical Study 2819-MA-1002 (EXTEND). The objective of 2819-MA-1002 was to evaluate whether the extended fidaxomicin therapy is superior to the standard vancomycin therapy in sustained clinical cure of CDI at 30 days after end of treatment (Day 40 or Day 55) in subjects that are ≥60 years of age.

For each patient a stool sample was collected at screening (Day 0) and also in case of disease recurrence or unscheduled visit. For subjects participating in the Microbiome sub-study stool samples were collected at Day 0 (screening), Day 5, Day 12, Day 27, Day 40, Day 55 and in the case of disease recurrence or an unscheduled visit. Samples were analysed on the BioFire FilmArray Instrument for the presence of toxigenic *C. difficile* targeting both the Toxin A gene and the Toxin B gene, and a number of other pathogens that may cause diarrhea using the FilmArray Gastrointestinal (GI) Panels [RFIT-ASY-0104] and RFIT-ASY-0116 as obtained from bioMérieux, (Basingstoke, UK).

Samples were tested for the presence of 22 targets. These targets are common gastrointestinal pathogens and include viruses, bacteria and parasites. Defrosted samples were homogenised in molecular grade water and analysed on the BioFire FilmArray Instrument one at a time.

The following targets were tested for: *Campylobacter* (*C. jejuni/C. coli/C. upsaliensis*), *Clostridium difficile* (*C. difficile*) toxin A/B, *Plesiomonas shigelloides, Salmonella, Vibrio* (*V. parahaemolyticus/V. vulnificus/V. cholera*), *Yersinia enterocolitica*, Enteroaggregative *Escherichia coli* (EAEC), Enteropathogenic *Escherichia coli*(EPEC), Enterotoxigenic *Escherichia coli* (ETEC) lt/st, Shiga-like toxin-producing *Escherichia coli* (STEC) stx1/stx2, *Escherichia coli* O157, *Shigella*/Enteroinvasive *Escherichia coli* (EIEC), *Cryptosporidium, Cyclospora cayetanensis, Entamoeba histolytica, Giardia lamblia* (also known as *G. intestinalis* and *G. duodenalis*), Adenovirus F 40/41, Astrovirus, Norovirus GI/GII, Rotavirus A, Sapovirus (Genogroups I. II, IV, and Human faecal samples from study 2819-MA-1002 were received from the central laboratory, BARC (Industriepark Zwijnaarde 3B B-9052 Gent, Bel-

TABLE 6

Summary of assessment CDI toxin in faecal stool samples

| Visit | Statistic/Category | Extended Fidaxomicin (n = 181) | Standard Vancomycin (n = 181) | Total (n = 362) |
| --- | --- | --- | --- | --- |
| Screening | n | 135 | 154 | 289 |
| | Positive | 94 (69.6%) | 106 (68.8%) | 200 (69.2%) |
| | Negative | 41 (30.4%) | 48 (31.2%) | 89 (30.8%) |
| Sub-study visit day 5 | n | 20 | 20 | 40 |
| | Positive | 5 (25%) | 5 (25.0%) | 10 (25.0%) |
| | Negative | 15 (75%) | 15 (75%) | 30 (75.0%) |
| Sub-study visit day 12 | n | 20 | 20 | 40 |
| | Positive | 1 (5.0%) | 0 | 1 (2.5%) |
| | Negative | 19 (95.0%) | 20 (100.0%) | 39 (97.5%) |
| Sub-study visit day 27 | n | 20 | 17 | 37 |
| | Positive | 1 (5.0%) | 3 (17.6%) | 4 (10.8%) |
| | Negative | 19 (95.0%) | 14 (82.4%) | 33 (89.2%) | gium). The samples were sent to LGC packed in dry ice and upon receipt stored in a freezer (nominally −80° C.).

EXAMPLE 5

Comparison of Various Fidaxomicin Treatment Regimens Compared to Standard Vancomycin Therapy

TABLE 7

Comparison of various fidaxomicin treatment regimens compared to standard vancomycin therapy

|  | Extended fidaxomicin[1] | | Standard fidaxomicin[2] | | Standard fidaxomicin[3] | |
| --- | --- | --- | --- | --- | --- | --- |
|  | FDX (n = 146) | VAN (n = 167) | FDX (n = 287) | VAN (n = 309) | FDX (n = 252) | VAN |
| Sustained clinical cure 30 days after end of treatment | 124/143 86.7% | 105/167 62.9% | 214/287 74.6% | 198/309 64.1% | 193/252 76.6% | 163/257 63.4% |
| Recurrence 30 days after end of treatment | 5/142 3.5% | 26/161 16.1% | 39/253 15.4% | 67/265 25.3% | 28/221 12.7% | 60/223 26.9% |

[1]Dosage regimen according to invention and as specified in Example 1, Table 1
[2]Louie T J, et al. N Engl J Med 2011; 364: 422-31; Dosage regimen: 200 mg Fidaxomicin twice daily or vancomycin 125 mg four times daily orally for 10 days
[3]Cornely O A, et al. Lancet Infect Dis 2012; 12: 281-9; Dosage regimen: 200 mg Fidaxomicin twice daily or vancomycin 125 mg four times daily orally for 10 days

EXAMPLE 6

A patient being tested positively for *Clostridium difficile* toxin A and B (using a suitable assay known in the art) and having >5 UBM per day is treated with 200 mg Fidaxomicin twice a day in an initial course of treatment. The number of UBM is monitored daily to establish if the number of UBM will change positively to ≤3 UBM per day. At day 2 of the initial course of treatment the UBM is reduced to 2 UBM per day and at day 3 to 1 UBM per day. Since the UBM is below 4 UBM per day and even below 3 UBM per day for 2 consecutive days, the dosage regimen is switched to the intermittent course of treatment by administering to the patient 200 mg Fidaxomicin every other day starting from day 5 until *Clostridium difficile* toxin A and B are tested negative. The presence of *Clostridium difficile* toxin A and B is tested negative at day 12 after start of treatment (using a suitable assay known in the art).

EXAMPLE 7

A patient being tested positively for *Clostridium difficile* toxin A and B (using a suitable assay known in the art) and having >5 UBM per day is treated with 200 mg Fidaxomicin twice a day in an initial course of treatment. The number of UBM is monitored daily to establish if the number of UBM will change positively to ≤3 UBM per day. At day 9 and 10 of the initial course of treatment the UBM is reduced to 3 UBM per day. Since the UBM is below 4 UBM per day for 2 consecutive days, the dosage regimen is switched to the intermittent course of treatment by administering to the patient 200 mg Fidaxomicin every other day starting from day 12 until *Clostridium difficile* toxin A and B are tested negative. The presence of *Clostridium difficile* toxin A and B is tested negative at day 27 after start of treatment (using a suitable assay known in the art).

EXAMPLE 8

Individual Patient Data for Extended Fidaxomicin Treatment Regimen

TABLE 8

Individual patient data

| Parameter | Patient 1 ID: 3000510001 | Patient 2 ID: 3000710001 | Patient 3 ID: 3400310001 | Patient 4 ID: 3580210001 |
| --- | --- | --- | --- | --- |
| Sex | Female | Female | Female | Male |
| Age in years | 77 | 86 | 78 | 94 |
| BMI in kg/m$^2$ | 19.1 | 25.7 | 26.0 | 23.1 |
| CDI severity at baseline | severe | non severe | severe | severe |
| Number of previous recurrences in the last three months prior to randomization | 0 | 0 | 0 | 2 |
| Use of antibiotics for conditions other than CDI prior to the study | yes | no | yes | no |
| Cancer | yes | yes | yes | yes |
| Charlson Co-Morbidity Index Score | 6 | 7 | 6 | 7 |
| Number of Unformed bowel movements per day | | | | |
| −1 | 5 | 5 | 10 | 6 |
| 1 | 4 | 7 | 8 | 9 |
| 2 | 2 | 7 | 0 | 9 |
| 3 | 1 | 2 | 0 | 5 |
| 4 | 0 | 1 | 0 | 3 |
| 5 | 0 | 1 | 0 | 2 |
| 6 | 2 | 2 | 0 | 3 |
| 7 | 0 | 1 | 0 | 3 |
| 8 | 0 | 1 | 0 | 1 |

TABLE 8-continued

Individual patient data

| Parameter | Patient 1 ID: 3000510001 | Patient 2 ID: 3000710001 | Patient 3 ID: 3400310001 | Patient 4 ID: 3580210001 |
|---|---|---|---|---|
| 9 | 0 | 1 | 0 | 1 |
| 10 | 0 | 0 | 0 | 2 |
| Clostridium difficile toxin A and B | Presence | Presence | Presence | Presence |
| Semi-quantitative* | 1.927 | 1.9008 | 2.6577 | 2.9786 |

*ratio of 2 measurements of the amount of light ($I/I_0$), the unit divides out

INDUSTRIAL APPLICABILITY

The treatment regimens with fidaxomicin compositions according to the present invention show many advantages.

The extension of the treatment duration period out from 10 to 20 or 25 days allows additional time for recovery of the patients colonic microflora which provides colonisation resistance against subsequent CDI relapse/recurrence without using additional medication.

Therefore the clear benefit of the dosing regimens according to the present invention over the 20 day twice daily regimen is that it provides equivalent efficacy in terms of reduction of *C. difficile* cells, spores and toxin while allowing recovery of the bowel flora which is expected to translate into a further reduction in the recurrence over the existing dose (200 mg BID during 10 days), but it does this using the standard 10 day pack of fidaxomicin tablets (DIFICLIR™) rather than having to use 2 packs.

If the proposed clinical study based on the results of the in vitro test will be successful then it will be obvious that where possible, the recommended dosing regimen will be changed from the twice daily 200 mg for 10 days regimen to the dosing regimens according to the present invention. The expected benefit to patients, doctors and society would be that reducing the recurrence to below 5% would significantly alter the cost effectiveness argument in fidaxomicin's favour.

The invention claimed is:

1. A method of treating *Clostridium difficile* infections (CDI) or *Clostridium difficile*-associated disease (CDAD) in a patient comprising oral administration of a tiacumicin compound, a stereo-isomer thereof, a polymorph thereof or a pharmaceutically acceptable solvate thereof according to a dosage regimen comprising: (1) administering to the patient in an initial course of treatment 200 mg of the tiacumicin compound twice a day; (2) monitoring the efficacy of the initial course of treatment in the patient by means of monitoring changes of one or more indicators of CDI or CDAD; (3) assessing whether there is a positive change of the one or the more of the indicators; and (4) switching to an intermittent course of treatment by administering to the patient 200 mg of the tiacumicin compound every other day for 7 days or more if the one or the more of the indicators of CDI or CDAD are positively changed, wherein the tiacumicin compound is fidaxomicin (C-19 R-tiacumicin B).

2. The method according to claim 1, wherein the one or the more indicators of CDI or CDAD are selected from the group consisting of (a) Frequency of diarrhea, (b) Consistency of stool (c) *Clostridium difficile* toxin B (TcdB toxin) and/or *Clostridium difficile* toxin A (TcdA toxin), (d) *Clostridium difficile* toxin B gene (tcdB) and (e) *Clostridium difficile* surface antigen (GDH).

3. The method according to claim 2, wherein the indicator of CDI or CDAD is the frequency of diarrhea.

4. The method according to claim 3, wherein the frequency of diarrhea is reduced to less than 4 unformed bowel movements (UBM) per day for 2 consecutive days.

5. The method according to claim 4, wherein the frequency of diarrhea is reduced to less than 3 unformed bowel movements (UBM) per day for 2 consecutive days.

6. The method according to claim 2, wherein the indicator of CDI or CDAD is the consistency of the stool.

7. The method according to claim 6, wherein the consistency of the stool shows an improvement from type 7 or type 6 to type 4 according to the Bristol stool form scale.

8. The method according to claim 2, wherein the indicator of CDI or CDAD is *Clostridium difficile* toxin B and/or *Clostridium difficile* toxin A (TcdA toxin) (TcdB toxin).

9. The method according to claim 8, wherein the *Clostridium difficile* toxin B (TcdB toxin) and/or the *Clostridium difficile* toxin A (TcdA toxin) is absent.

10. The method according to claim 2, wherein the indicator of CDI or CDAD is the *Clostridium difficile* toxin B gene (tcdB).

11. The method according to claim 10, wherein the *Clostridium difficile* toxin B gene (tcdB) is absent.

12. The method according to claim 2, wherein the indicator of CDI or CDAD is the *Clostridium difficile* surface antigen glutamate dehydrogenase (GDH).

13. The method according to claim 12, wherein the *Clostridium difficile* surface antigen glutamate dehydrogenase (GDH) is absent.

14. The method according to claim 1, wherein the initial course of treatment lasts for 5 days.

15. The method according to claim 1, wherein the initial course of treatment lasts for 3 to 10 days.

16. The method according to claim 1, wherein the intermittent course of treatment lasts for 20 days.

17. The method according to claim 1, wherein the dosage regimen further comprises 5) monitoring one or more indicators of gut microflora, and 6) discontinuing the intermittent course of treatment if the one or the more of the indicators of gut microflora have favourably changed.

18. The method according to claim 17, wherein the indicator of gut microflora is the *Enterobacteriaceae* count.

19. The method according to claim 18, wherein the total *Enterobacteriaceae* count of gut microflora is 90% reduced compared to the level prior to the initial course of treatment.

20. The method according to claim 1, wherein the recurrence of CDI or CDAD in a patient is below 10% 30 days after end of treatment.

21. The method according to claim 1, wherein the recurrence of CDI or CDAD in a patient is below 5% 30 days after end of treatment.

* * * * *